United States Patent [19]
Takatani et al.

[11] Patent Number: 5,490,506
[45] Date of Patent: Feb. 13, 1996

[54] PERIPHERAL BLOOD FLOW EVALUATING APPARATUS

[75] Inventors: Setsuo Takatani, Houston, Tex.; Hiroshi Sakai, Komaki, Japan

[73] Assignee: Colin Corporation, Aichi, Japan

[21] Appl. No.: 218,811

[22] Filed: Mar. 28, 1994

[51] Int. Cl.$^6$ ........................................... A61B 5/00
[52] U.S. Cl. ........................ 128/633; 128/665; 128/666; 128/689; 356/41
[58] Field of Search ........................... 128/633–634, 128/664–666, 687–691; 356/41

[56] References Cited

U.S. PATENT DOCUMENTS

| | | | |
|---|---|---|---|
| 3,769,974 | 11/1973 | Smart et al. | |
| 4,545,387 | 10/1985 | Balique | 128/688 |
| 4,867,557 | 9/1989 | Takatani et al. | |
| 5,007,423 | 4/1991 | Branstetter et al. | 128/633 |
| 5,047,627 | 9/1991 | Yim et al. | 128/634 |
| 5,057,695 | 10/1991 | Hirao et al. | 128/633 |
| 5,188,108 | 2/1993 | Secker | 128/633 |
| 5,190,047 | 3/1993 | Odagiri et al. | 128/689 |
| 5,203,342 | 4/1993 | Sakai | 128/691 |

*Primary Examiner*—Angela D. Sykes
*Assistant Examiner*—Robert L. Nasser, Jr.
*Attorney, Agent, or Firm*—Oliff & Berridge

[57] ABSTRACT

An apparatus for evaluating a peripheral blood flow of a living subject, including a reflection-type pulse wave detecting device including two pairs of light-emitting and light-receiving elements provided such that a distance between the light-emitting and light-receiving elements of one pair is different from that of the other pair; and a determining device for determining an attenuation coefficient of the light beam emitted by the light-emitting element of each pair, based on (a) an intensity of the light beam which is emitted by the light-emitting element of each pair and (b) an intensity of the light which has been emitted from the light-emitting element of each pair, reflected from skin of the subject, and subsequently received by the light-receiving element of each pair. The apparatus further includes an evaluating device for evaluating peripheral blood flow of the subject, based on a ratio of the attenuation coefficient of the light beam emitted by the light-emitting element of one pair to the attenuation coefficient of the light beam emitted by the light-emitting element of the other pair, and/or, a display which displays a change of the ratio of the attenuation coefficient of the light beam emitted by the light-emitting element of one pair to the attenuation coefficient of the light beam emitted by the light-emitting element of the other pair.

22 Claims, 5 Drawing Sheets

PERIPHERAL BLOOD FLOW EVALUATING APPARATUS

BACKGROUND OF THE INVENTION

1. Field of the Invention

The present invention relates to an apparatus for evaluating the peripheral blood flow of a living body or subject such as a patient.

2. Related Art Statement

Since the color and/or temperature of skin of a patient indicates the peripheral blood flow of the patient, an anesthesiologist checks by using his or her sensation those indications at intervals of time for identifying whether the patient, e.g., under a surgical operation has fallen in a shock due to, e.g., an abrupt decrease of blood pressure. However, since this method depends on sensations of doctors, it needs doctors' experiences and suffers from their individual differences. Additionally, since doctors use this method while referring to blood pressure reading of a blood pressure machine, it needs a considerably long time to identify a patient's shock.

In the above background of art, U.S. Pat. No. 3,769,974 discloses a reflection-type pulse wave detecting device (i.e., plethysmograph) which is basically directed to the measurement of pulse rate of a living body. The pulse wave detecting device detects the variation of intensity of the reflected light from the tissue of skin of the living body, i.e., volume pulse wave resulting from flowing of blood in the skin tissue. Since an arterial network extending in dermis under epidermis of the skin contracts when the living body falls into a shock, the volume pulse wave detected by the prior device may change (i.e., decrease) in response to the shock of the living body.

The above reflection-type pulse wave detecting device includes (a) a light emitting element which emits a light beam toward the skin, and (b) a light receiving element which is provided at a predetermined distance from the light emitting element and which receives the light which has been emitted from the light emitting element and subsequently reflected from the skin tissue. The light receiving element generates a reflected-light signal representing the reflected light received from the skin tissue. Since the reflected light from the skin tissue contains a volume pulse wave due to blood flow produced in the skin tissue in synchronism with heartbeat of the living body, the reflected-light signal from the light receiving element represents the volume pulse wave of the living body. The reflected-light signal or volume-pulse-wave signal may change due to patient's shock. However, the reflected-light signal is also influenced by other factors such as air temperature, intensity of the light beam emitted by the light emitting element, or mental condition of the patient. Thus, the reflected-light signal produced by the prior device cannot be used for identifying an abnormality of peripheral blood flow of a patient.

SUMMARY OF THE INVENTION

It is therefore an object of the present invention to provide an apparatus for accurately evaluating a peripheral blood flow of a living body or subject such as a patient, thereby finding a shock of the subject.

The above object may be achieved according to a first aspect of the present invention, which provides an apparatus for evaluating a peripheral blood flow of a living subject, comprising: a reflection-type pulse wave detecting device including at least two pairs of light-emitting and light-receiving elements provided such that a distance between the light-emitting and light-receiving elements of one of the at least two pairs is different from a distance between the light-emitting and light-receiving elements of the other, or each of the others, of the at least two pairs, the at least two pairs of light-emitting and light-receiving elements being adapted to be opposed to a skin of the subject, so that the light-emitting element of each of the at least two pairs emits a light beam toward the skin and so that the light-receiving element of the each pair receives the light which has been emitted from the light-emitting element of the each pair and subsequently reflected from the skin, and generates a reflected-light signal representing the reflected light received from the skin and containing a pulse wave resulting from flowing of blood in the skin; attenuation-coefficient determining means for determining an attenuation coefficient of the light beam emitted by the light-emitting element of the each pair, based on (a) an intensity of the light beam which is emitted by the light-emitting element of the each pair and (b) an intensity of the light which has been emitted from the light-emitting element of the each pair, reflected from the skin of the subject, and subsequently received by the light-receiving element of the each pair; and peripheral-blood-flow evaluating means for evaluating the peripheral blood flow of the subject, based on a ratio of the attenuation coefficient of the light beam emitted by the light-emitting element of one of the at least two pairs, to the attenuation coefficient of the light beam emitted by the light-emitting element of the other or another of the at least two pairs.

In the peripheral blood flow evaluating apparatus constructed as described above, two or more pairs of light-emitting and light-receiving elements are provided such that the distance between the light-emitting and light-receiving elements of one of the pairs is different from the distance between the light-emitting and light-receiving elements of the other pair or each of the other pairs. Therefore, the reflection-type pulse wave detecting device receives two or more reflected lights from two or more depths in the skin tissue of the subject. The attenuation-coefficient determining means determines an attenuation coefficient of the light beam emitted by the light-emitting element of each of the pairs, and the peripheral-blood-flow evaluating means evaluates the peripheral blood flow of the subject, based on a ratio of the attenuation coefficient of the light beam emitted by the light-emitting element of one of the pairs, to the attenuation coefficient of the light beam emitted by the light-emitting element of the other pair or another of the other pairs. An attenuation coefficient determined by the attenuation-coefficient determining means corresponds to an instantaneous degree of light absorption and diffusion characteristics of a portion of the skin tissue which reflects (i.e., diffuses) a light beam, i.e., an instantaneous volume of blood existing in that portion of the skin tissue. Therefore, the ratio of two attenuation coefficients determined with respect to two light beams shows a difference between the instantaneous volumes of blood existing in two portions of different depths in the skin tissue which respectively reflect the two light beams. The attenuation coefficient ratio is not influenced by any of those factors which influence both of the respective blood volumes in the two depth-different portions of the skin tissue; such as air temperature, intensity of the light beam or beams used, or mental condition of the subject. On the other hand, the attenuation coefficient ratio responds to a patient's shock involving contraction of blood vessels of his or her peripheral tissues. The attenuation coefficient ratio is preferable to the difference between the two attenuation coefficients.

The above object may also be achieved according to a second aspect of the present invention, which provides an apparatus for evaluating a peripheral blood flow of a living subject, comprising: a reflection-type pulse wave detecting device including at least two pairs of light-emitting and light-receiving elements provided such that a distance between the light-emitting and light-receiving elements of one of the at least two pairs is different from a distance between the light-emitting and light-receiving elements of the other, or each of the others, of the at least two pairs, the at least two pairs of light-emitting and light-receiving elements being adapted to be opposed to a skin of the subject, so that the light-emitting element of each of the at least two pairs emits a light beam toward the skin and so that the light-receiving element of the each pair receives the light which has been emitted from the light-emitting element of the each pair and subsequently reflected from the skin, and generates a reflected-light signal representing the reflected light received from the skin and containing a pulse wave resulting from flowing of blood in the skin; attenuation-coefficient determining means for determining an attenuation coefficient of the light beam emitted by the light-emitting element of the each pair, based on (a) an intensity of the light beam which is emitted by the light-emitting element of the each pair and (b) an intensity of the light which has been emitted from the light-emitting element of the each pair, reflected from the skin of the subject, and subsequently received by the light-receiving element of the each pair; and a display which displays a change of a ratio of the attenuation coefficient of the light beam emitted by the light-emitting element of one of the at least two pairs, to the attenuation coefficient of the light beam emitted by the light-emitting element of the other or another of the at least two pairs.

In the peripheral blood flow evaluating apparatus in-accordance with the second aspect of the invention, the display indicates a time-wise change of the attenuation coefficient ratio, which is advantageously available to medical staff for monitoring a patient's shock.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings in which.

DETAILED DESCRIPTION OF THE PREFERRED EMBODIMENTS

Figure 1:
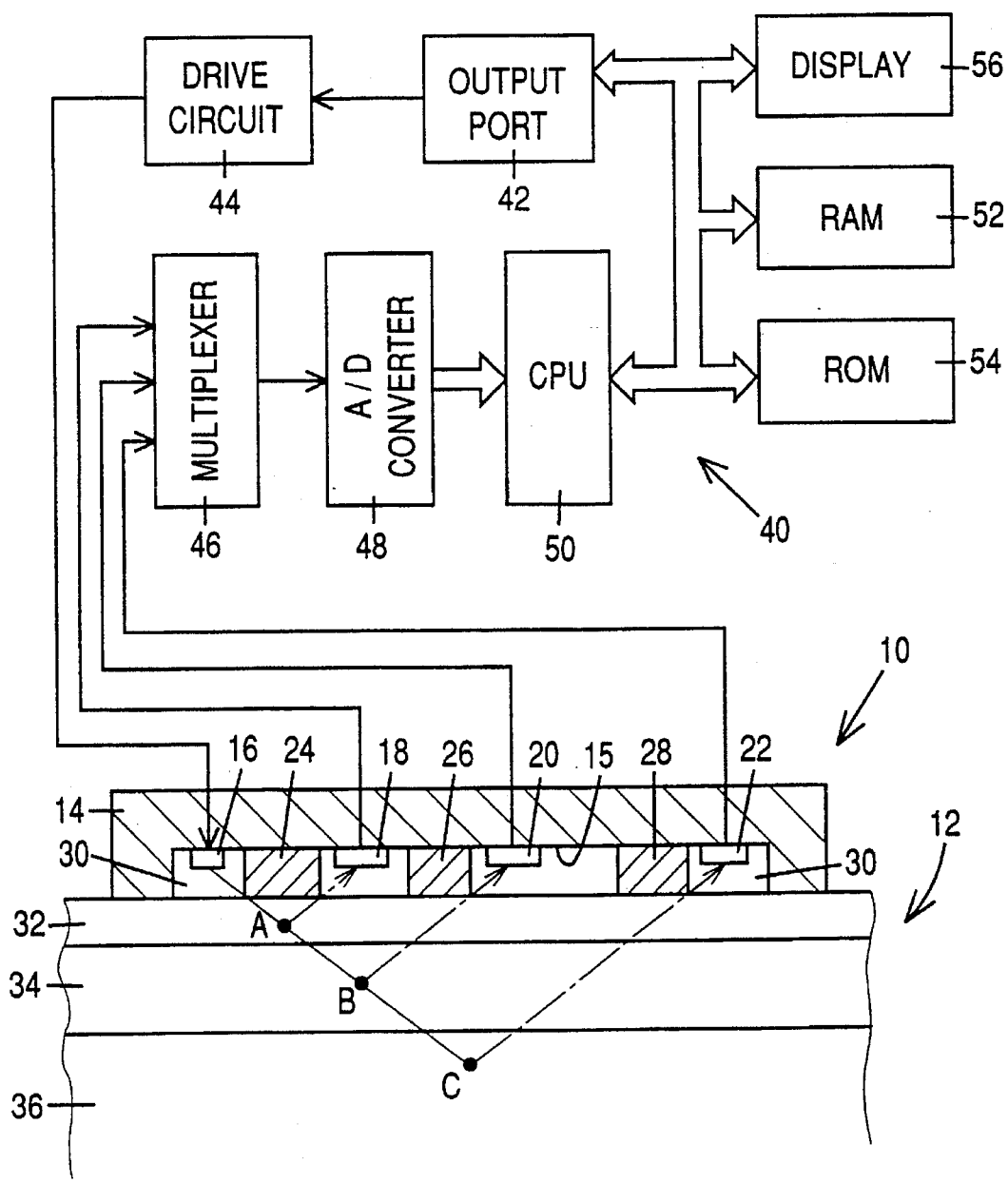
FIG. 1 is a diagrammatic view of a peripheral blood flow evaluating apparatus to which the present invention is applied.

Referring first to FIG. 1, there is shown a peripheral blood flow evaluating apparatus to which the present invention is applied.

In FIG. 1, reference numeral 10 designates a reflection-type pulse wave (PW) sensor which is adapted to be set on a skin 12 of a living subject such as a patient with the help of a setting device (not shown) such as a pair of bands or a double-coated adhesive sheet. The PW sensor 10 includes a housing 14 having a recess 15. The PW sensor 10 further includes a common light emitting element 16, and a first, a second, and a third light receiving element 18, 20, 22. The light emitting element 16 is, for example, a light emitting diode (LED) chip. Each of the first to third light receiving elements 18, 20, 22 is, for example, a well-known photo-diode or phototransistor chip. The four chips 16, 18, 20, 22 are received in the recess 15 of the housing 14. The housing 14 has a first, a second, and a third light shading wall 24, 26, 28 each of which is disposed between corresponding adjacent two chips of the four chips 16, 18, 20, 22. A transparent resin 30 fills a vacant space remaining in the recess 15. With the PW sensor 10 being set on the skin 12, the transparent resin 30 is held in contact with the skin surface 12 and the four chips 16, 18, 20, 22 are opposed to the skin surface 12. The distances between the light emitting element 16 and each of the three light 10 receiving elements 18, 20, 22 are pre-selected at respective values different from each other.

When the common light emitting element 16 emits a light beam toward the skin 12, the light beam is reflected (i.e., scattered or diffused) by the skin tissue 12 and subsequently received by each of the three light receiving elements 18, 20, 22. In the present embodiment, the common light emitting element 16 and the three light receiving elements 18, 20, 22 provide three pairs of light emitting and light receiving elements. The common light emitting element 16 serves as the light emitting element of each of the three pairs.

The skin tissue 12 includes (a) an epidermis 32 that is an exposed corneal layer and has a thickness of about 0.1 mm to 0.3 mm, (b) a dermis 34 that exists under the epidermis 32 and has a thickness of about 0.3 mm to 2.4 mm, and a subcutaneous tissue 36 that exists under the dermis 34 and contains a plenty of fat. Generally there is no clear boundary between the dermis 34 and subcutaneous tissue 36. An arterial network extends from around the boundary of dermis and subctaneous tissue 34, 36 into the dermis layer 34. The small arteries of the arterial network terminate into capillaries, a portion of which run into papillae of hair roots. Then, blood flows into veins in a venous network extending from the dermis layer 34 into the boundary of dermis and subctaneous tissue 34, 36. A portion of the small veins of the venous network join to deep veins running along arteries, and another-portion of the veins join to cutaneous veins.

The respective positions of the four chips 16, 18, 20, 22 received in the recess 15 of the housing 14, and the respective shapes (i.e., dimensions) and positions of the three walls 24, 26, 28, are pre-determined so that the first light receiving element 18 receives a first reflected light from a first point or depth, A (FIG. 1), located in the epidermis layer 32, the second light receiving element 20 receives a second reflected light from a second point or depth, B, in the dermis layer 34, and the third light receiving element 22 receives a third reflected light from a third point or depth, C, in the subcutaneous tissue 36. Thus, the second depth B is smaller than the first depth A and greater than the third depth C.

The common light emitting element 16 emits a red or infrared light having a wavelength not smaller than 660 nm that has a characteristic of being easily diffused by red blood cells existing in the skin tissue 12. Preferably, the LED chip 16 emits an about 805 nm infrared light falling within a specific range of wavelengths whose intensities are not easily, influenced by variation of the oxygen saturation of blood.

The present apparatus also includes an arithmetic and control device 40 which outputs, via an output port 42, a command signal to a drive circuit 44. Responsive to the command signal, the drive circuit 44 supplies an electric current to the LED chip 16, so that the LED chip 16 emits a light beam toward the skin 12. The first to third light receiving elements 18, 20, 22 receive the first to third reflected lights from the first to third points (depths) A, B, C of the skin tissue 12, respectively, and generate respective reflected-light signals representing the first to third reflected lights. Each of the three reflected-light signals contains a volume pulse wave signal resulting from pulsatile blood flow produced in the skin tissue in synchronism with heartbeat of the subject. The three reflected-light signals are transmitted via an amplifier (not shown) to a multiplexer 46 and subsequently to an analog to digital (A/D) converter 48. The thus digitized signals are fed to a central processing unit (CPU) 50 of the control device 40. The control device 40 additionally includes a random access memory (RAM) 52 and a read only memory (ROM) 54, and processes input signals according to control programs pre-stored in the ROM 54 by utilizing a temporary-data- storage function of the RAM 52. The CPU 50 commands a display 56 to indicate the processed data or result.

Hereinafter, there will be described the operation of the peripheral blood flow evaluating apparatus constructed as described above, by reference to the flow chart of FIG. 2.

First, at Step S1, the CPU 50 commands the drive circuit 44 to cause the LED chip 16 to emit a light beam toward the skin 12, and receives the first to third reflected-light signals from the first to third light receiving chips 18, 20, 22, respectively. Step S1 is followed by Step S2 to determine an intensity, $I_{R1}$, of the first reflected light represented by the first reflected-light signal from the first light receiving chip 18, an intensity, $I_{R2}$, of the second reflected light represented by the second reflected light signal from the second light receiving chip 20, and an intensity, $I_{R3}$, of the third reflected light represented by the third reflected light signal from the third light receiving chip 22. The CPU 50 further calculates, based on the thus determined three intensities $I_{R1}$, $I_{R2}$, $I_{R3}$, a first attenuation coefficient, $K_1$, of the first reflected light, a second attenuation coefficient, $K_2$, of the second reflected light, and a third attenuation coefficient, $K_3$, of the third reflected light, according to the following first, second, and third expressions (1), (2), and (3), respectively:

$$K_1 = I_{R1}/I_O \quad (1)$$

$$K_2 = (I_{R2}/I_O)/(I_{R1}/I_O)^2 \quad (2)$$

$$K_3 = (I_{R3}/I_O)(I_{R1}/I_O)^2/(I_{R2}/I_O)^2 \quad (3)$$

, where $I_O$: a pre-selected intensity (i.e., constant value) of a light beam which is emitted by the LED chip 16.

Figure 3:
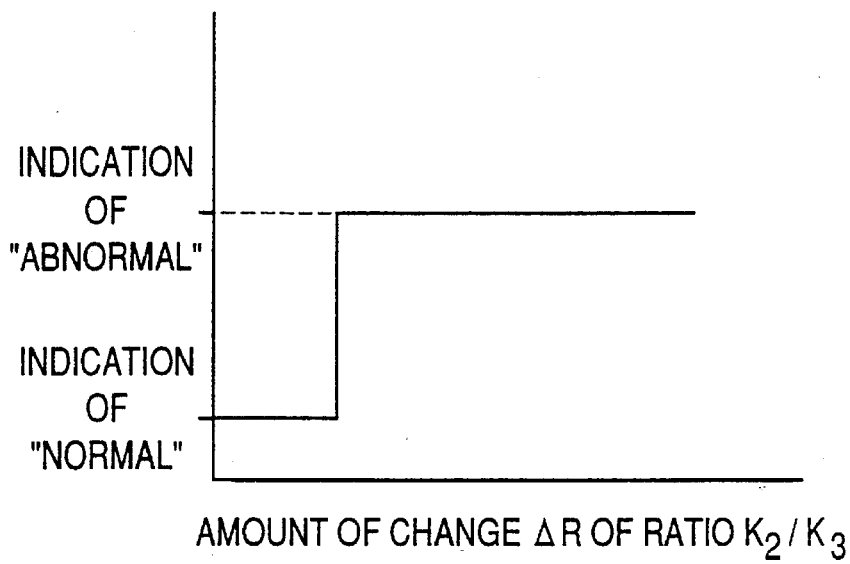
FIG. 3 is a view showing a relationship used by the apparatus of FIG. 1 for evaluating the peripheral blood flow of a living subject.

Subsequently, at Step S3, the CPU 50 calculates a ratio of the second coefficient $K_2$ to the third coefficient $K_3$. Step S3 is followed by Step S4 to calculate an amount of change, $\Delta R$, of the ratio $K_2/K_3$ determined in the current control cycle, from that determined in a prior control cycle before a predetermined period of time (e.g., several seconds). Based on the amount of change $\Delta R$, the CPU 50 judges whether the peripheral blood flow of the subject is normal or abnormal, according to the relationship shown in FIG. 3. At the following step, Step S5, the CPU 50 commands the display 56 to indicate the attenuation coefficients $K_1$, $K_2$, $K_3$ and ratio $K_2/K_3$ obtained at Steps S2 and S3, as the current values of their time-wise varying trends or curves. The CPU 50 also commands the display 56 to indicate the result of judgment obtained at Step S4.

Figure 4:
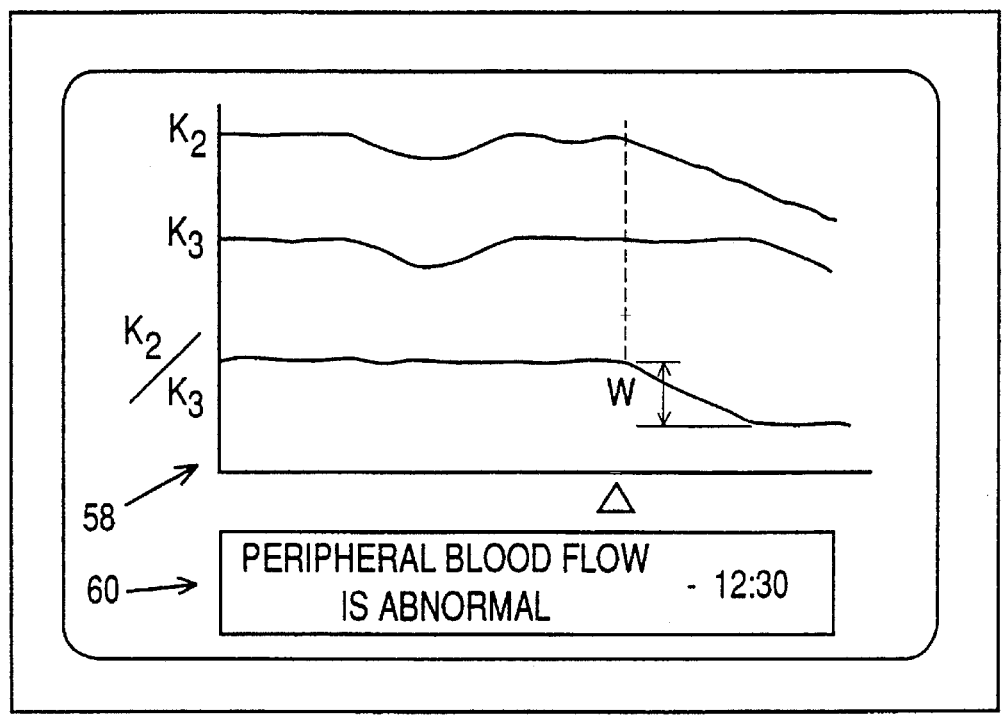
FIG. 4 is a view of an example of a display employable in the apparatus of FIG. 1.

FIG. 4 shows an example of the display 56 employable in the present apparatus. The display 56 includes a first display section 58 for providing respective graphical presentations of the attenuation coefficients $K_2$, $K_3$ and attenuation-coefficient ratio $K_2/K_3$, and a second display section 60 for indicating an evaluation result, either "PERIPHERAL BLOOD FLOW IS NORMAL" or "PERIPHERAL BLOOD FLOW IS ABNORMAL", together with a time of day when a judgment is made at Step S4. A triangle shown in the first display section 58 indicates the time when a normality judgment has last been changed to an abnormality judgement at Step S4. In the present embodiment, Step S2 and a portion of the control device 40 to carry out the step cooperate with each other to provide attenuation-coefficient determining means. Meanwhile, Steps S3 and S4 and a portion of the control device 40 to carry out those steps cooperate with each other to provide peripheral-blood-flow evaluating means.

As emerges from the foregoing description, in the present apparatus, the PW sensor 20 includes two pairs of light emitting and receiving elements (16, 20), (16, 22) such that the distance between the light emitting and receiving elements 16, 20 is different from the distance between the light emitting and receiving elements 16, 22. Therefore, the two light receiving elements 20, 22 receive the different reflected lights from the respective points B, C of different depths as measured from the exposed surface of the epidermis 32. At Step S2, the CPU 50 calculates the attenuation-coefficient ratio $K_2/K_3$ based on the intensities $I_{R2}$, $I_{R3}$ of those different reflected lights. Then, at Step S4, the CPU 34 judges whether the peripheral blood flow of the subject is normal or abnormal, based on an amount of change $\Delta R$ of the ratio $K_2/K_3$. At Step S5, the CPU 50 commands the display 56 to indicate the normality or abnormality judgement made at Step S4, and the ratio $K_2/K_3$ obtained at Step S3 as the current value of its time-wise variable curve. From the graphical presentation of the ratio $K_2/K_3$ provided in the first area 58 of the display 56, a doctor or other medical persons can read a total amount of change, W (FIG. 4), of the ratio $K_2/K_3$ from a reference value at the beginning of the change (e.g., value corresponding to the last normality judgment).

The intensity $I_{R2}$ of the second reflected light contains a variation of the light absorption and diffusion characteristics of the portion B (i.e., of the dermis 34), mainly, variation of the volume of the blood flowing through the portion B. Similarly, the intensity $I_{R3}$ of the third reflected light contains a variation of the light absorption and diffusion characteristics of the portion C (i.e., of the subcutaneous tissue 36) whose depth is greater than that of the portion B, mainly, variation of the volume of the blood flowing through the portion C. Each of the intensities $I_{R2}$, $I_{R3}$ contains a volume pulse wave resulting from blood flow produced in the skin tissue 12 in synchronism with heartbeat of the subject. Thus, the attenuation-coefficient ratio $K_2/K_3$ represents an instantaneous difference between the volume of blood existing in the portion B and the volume of blood existing in the portion C. Therefore, the ratio $K_2/K_3$ is not influenced by any of the factors, such as air temperature, intensity of the light beam emitted by the LED chip 16, or mental condition of the subject, each of which influences both the volume of blood existing in the portion B and the volume of blood existing in the portion C. On the other hand, when the patient falls into a shock which involves contraction of blood vessels of his or her peripheral tissues, the ratio $K_2/K_3$ responds and changes as indicated by the display 56 of FIG. 4. The present apparatus quickly and accurately identifies the patient's shock, and indicates the abnormality judgment on the second section 60 of the display 56 and the total change amount W of the ratio $K_2/K_3$ on the first display section 58. Thus, the present apparatus provides an accurate evaluation of peripheral blood flow of the subject.

Figure 5:
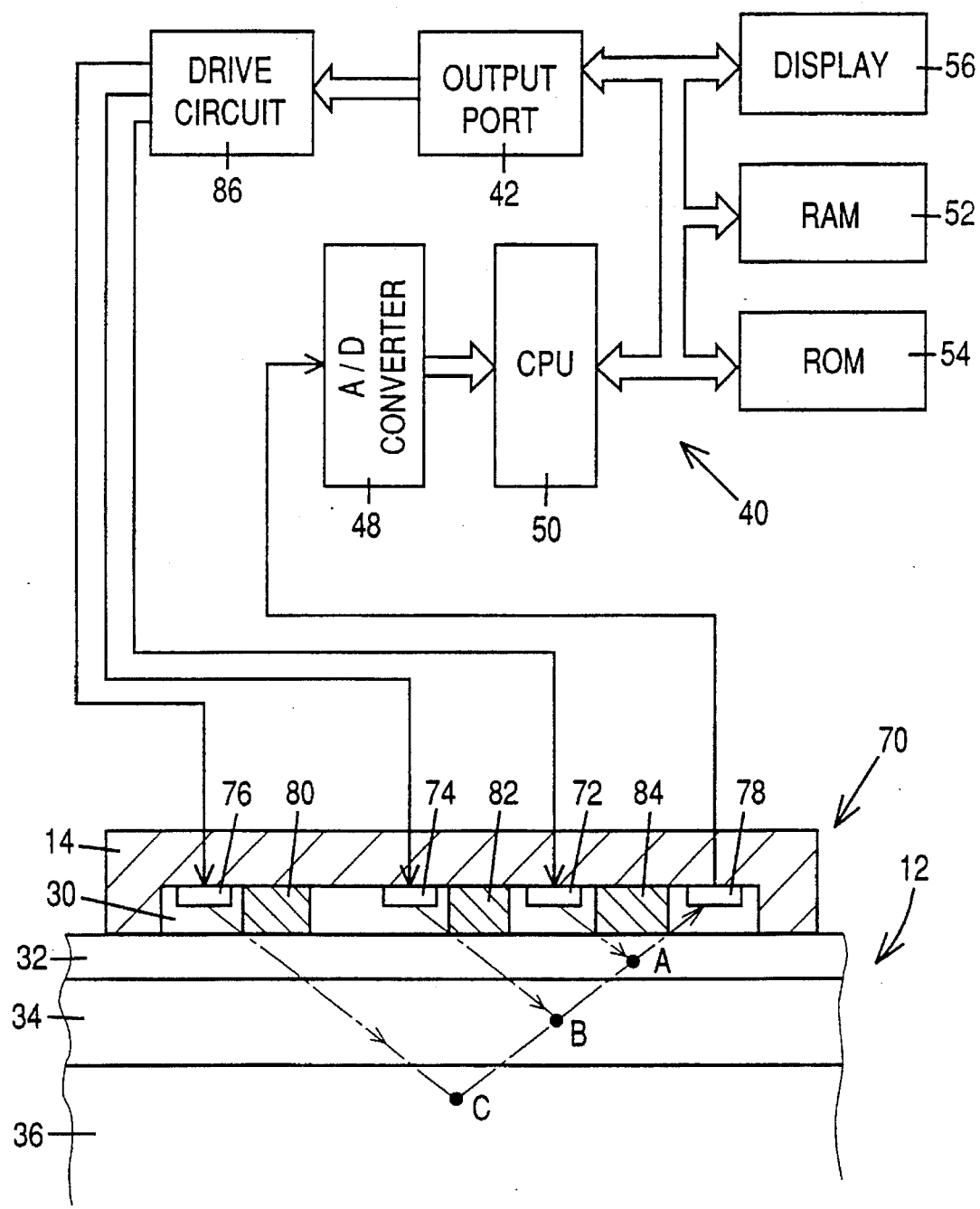
FIG. 5 is a diagrammatic view corresponding to FIG. 1, of a second embodiment of the invention.

Referring next to FIG. 5, there is shown a second embodiment of the present invention. The second embodiment also relates to a peripheral blood flow evaluating apparatus. The same reference numerals as used to designate the elements or parts of the first embodiment of FIG. 1 are used to designate the corresponding elements or parts of the second embodiment, and description thereof is omitted.

As shown in FIG. 5, the instant apparatus has a reflection-type pulse wave (PW) sensor 70 including a first, a second, and a third light emitting element 72, 74, 76 each of which emits a light beam having a wavelength equal to that of the light beam emitted by the LED chip 16 of the first embodiment, toward a skin 12 of a living subject. The PW sensor 70 also includes a common light receiving element 78 which receives the respective lights which have been emitted from the first, second, and third light emitting elements 72, 74, 76 and subsequently reflected (i.e., diffused) from a subcutaneous tissue 36, a dermis 36, and an epidermis 34 of the skin tissue 12, respectively. The PW sensor 72 additionally includes a housing 14 in which a first, a second, and a third light-shading wall 80, 82, 83 are disposed between the three light emitting elements 76, 74, 72 and the light receiving element 78. Each of the light emitting elements 72, 74, 76 is, for example, an LED chip. The single light receiving element 78 is, for example, a well-known photodiode or phototransistor chip. The distances between the common light receiving element 78 and each of the three light emitting elements 72, 74, 76 are pre-selected at respective values different from each other. Like the PW sensor 10 of the first embodiment of FIG. 1, the respective positions of the four chips 72, 74, 76, 78 in the housing 14 and the respective shapes (i.e., dimensions) and positions of the three walls 80, 82, 84 are pre-determined so that the common light receiving element 78 receives a first reflected light which has been emitted from the first LED chip 72 and subsequently reflected from a first point or depth, A (FIG. 5), located in the epidermis 32, receives a second reflected light which has been emitted from the second LED chip 74 and subsequently reflected from a second point or depth, B, in the dermis 34, and receives a third reflected light which has been emitted from the third LED chip 76 and subsequently reflected from a third point or depth, C, in the subcutaneous tissue 36.

The instant apparatus further includes a drive circuit 86 which selectively operates, by time sharing, the first to third LED chips 72, 74, 76 so that the three chips 72, 74, 76 sequentially emit respective light beams toward the skin 12. An arithmetic and control device 40 of the apparatus supplies command signals to the drive circuit 86 to operate the three LED chips 72, 74, 76 in the above manner. Consequently, the common light receiving element 78 sequentially receives the first, second, and third reflected lights from the three points A, B, C of different depths from the exposed surface of the epidermis 32, and sequentially generates three reflected-light signals representing the intensities of the received three reflected lights, to a central processing unit (CPU) 50 of the control device 40 via an amplifier (not shown) and an analog to digital (A/D) converter 48. The instant apparatus operates according to a control program similar to that represented by the flow chart of FIG. 2, and a display 56 provides presentations as shown in FIG. 4. Thus, the apparatus enjoys the same advantages as those of the first embodiment of FIG. 1.

Provided that the intensities of three light beams which are emitted by the three LED chips 72, 74, 76 be pre-selected at respective constant values, $I_{01}$, $I_{02}$, $I_{03}$, and that the intensities of the first to third reflected lights received by the common light receiving element 78 be expressed by respective symbols, $I_{R1}$, $I_{R2}$, $I_{R3}$, the CPU 34 calculates a first attenuation coefficient, $K_1$, of the first reflected light, a second attenuation coefficient, $K_2$, of the second reflected light, and a third attenuation coefficient, $K_3$, of the third reflected light, according to the following fourth, fifth, and sixth expressions (4), (5), and (6), respectively:

$$K_1 = I_{R1}/I_{01} \quad (4)$$

$$K_2 = (I_{R2}/I_{02})/(I_{R1}/I_{01})^2 \quad (5)$$

$$K_3 = (I_{R3}/I_{03})(I_{R1}/I_{01})^2/(I_{R2}/I_{02})^2 \quad (6)$$

The CPU 34 calculates a ratio, $K_2/K_3$, based on the thus determined values $K_2$, $K_3$.

Figure 6:
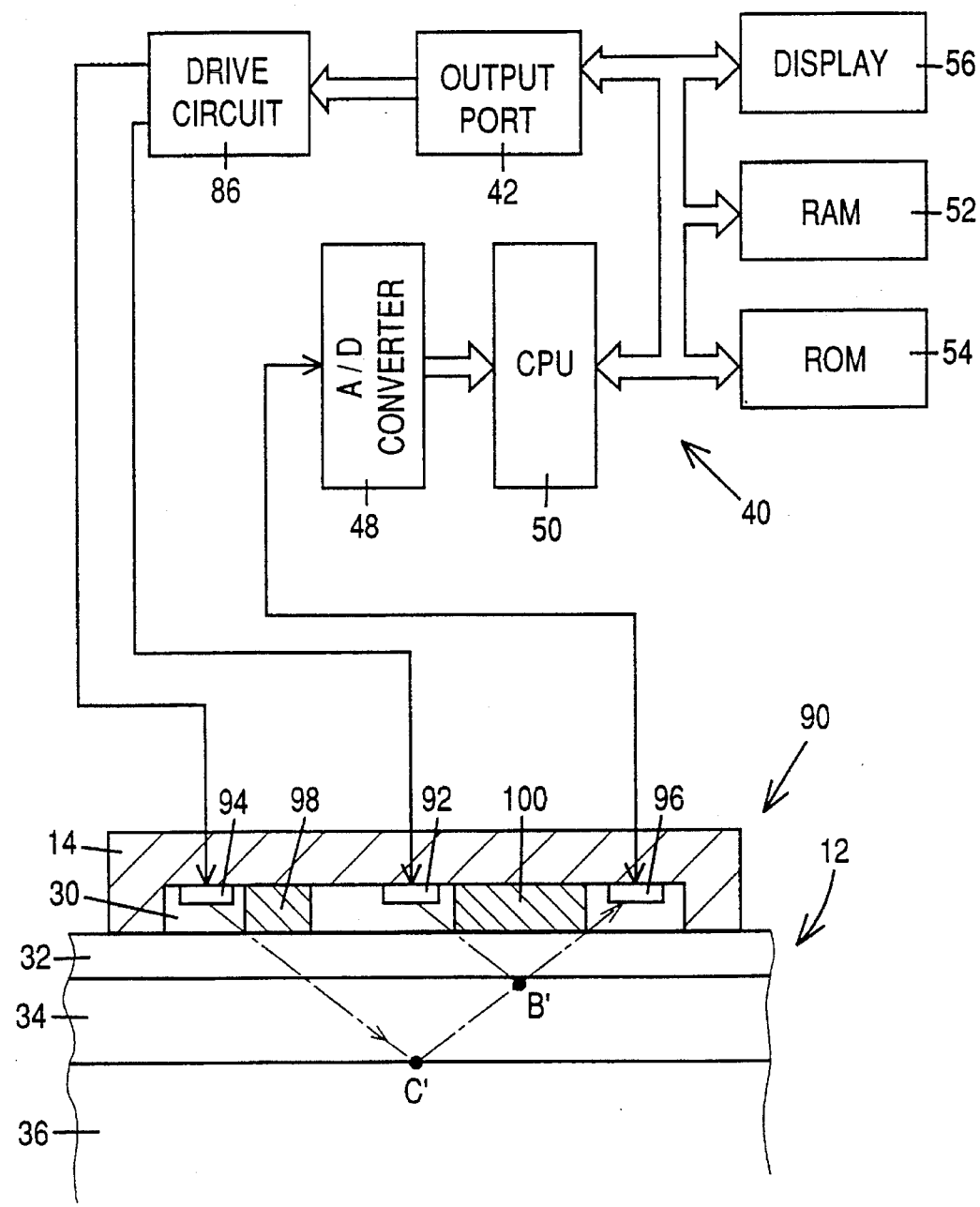
FIG. 6 is a diagrammatic view corresponding to FIG. 5, of a third embodiment of the invention.

Referring next to FIG. 6, there is shown a third embodiment of the present invention, which also relates to a peripheral blood flow evaluating apparatus. The same reference numerals as used to designate the elements or parts of the second embodiment of FIG. 5 are used to designate the corresponding elements or parts of the third embodiment, and description thereof is omitted.

As shown in FIG. 6, a reflection-type pulse wave (PW) sensor 90 of the apparatus includes a first and a second light emitting element 92, 94 each of which emits a light beam having a wavelength equal to that of the light beam emitted by the LED chip 16 of the first embodiment, toward a skin 12 of a subject. The PW sensor 90 also includes a common light receiving element 96 which receives the respective lights which have been emitted from the first and second light emitting elements 92, 94 and subsequently reflected from the skin tissue 12. The PW sensor 90 additionally includes a housing 14 in which a first and a second light-shading wall 98, 100 are disposed between the two light emitting elements 94, 92 and the light receiving element 96.

The distances between the light receiving element 96 and each of the two light emitting elements 92, 94 are pre-selected at respective values different from each other. The respective positions of the three elements 92, 94, 96 in the housing 14 and the respective shapes (i.e., dimensions) and positions of the two walls 98, 100 are pre-determined so that the common light receiving element 96 receives a first reflected light which has been emitted from the first LED chip 92 and subsequently reflected from a first point or depth, B'(FIG. 6), located in either (a) the epidermis and dermis 32, 34 or (b) the dermis layer 34, and receives a second reflected light which has been emitted from the second LED chip 94 and subsequently reflected from a second point or depth, C', located in either (b) the dermis layer 34 or (c) in the dermis and subcutaneous tissue 34, 36. The instant apparatus operates according to a control program similar to that represented by the flow chart of FIG. 2, and a display 56 provides presentations as shown in FIG. 4. Thus, the present apparatus enjoys the same advantages as those of the first embodiment of FIG. 1.

Provided that the intensities of two light beams which are emitted by the two LED chips 92, 94 be pre-selected at respective constant values, $I_{01}'$, $I_{02}'$, and that the intensities of the first and second reflected lights received by the common light receiving element 96 be expressed by respective symbols, $I_{R1}'$, $I_{R2}'$, the CPU 50 calculates a first attenuation coefficient, $K_1'$, of the first reflected light, and a second attenuation coefficient, $K_2'$, of the second reflected light, according to the following seventh and eighth expressions (7) and (8), respectively:

$$K_1' = I_{R1}'/I_{o1}' \qquad (7)$$

$$K_2' = (I_{R2}'/I_{o2}')/(I_{R1}'/I_{o1}')^2 \qquad (8)$$

The CPU 50 calculates a ratio, $K_1'/K_2'$, based on the thus determined values $K_1'/K_2'$, judges whether the peripheral blood flow of the subject is abnormal, based on the ratio $K_1'/K_2'$, and displays a graphical presentation of ratio $K_1'/K_2'$ on the display 56.

While the present invention has been described in its preferred embodiments, the invention may otherwise be embodied.

For example, while in the first and second embodiments the common light emitting element 16 or the common light receiving element 78 is used for the three pairs of light emitting and receiving elements constituted by the four elements (16, 18, 20, 22) or (72, 74, 76, 78), it is possible to employ three light emitting elements and three light receiving elements to provide three pairs of light emitting and receiving elements. This may apply to the third embodiment of FIG. 6 wherein two pairs of light emitting and receiving elements are constituted by the three elements 92, 94, 96. In the former case, the distance between the light emitting and light receiving elements of each of the three pairs is different from that of each of the other two pairs. In the latter case, the distance between the light emitting and light receiving elements of one of the two pairs is different from that of the other pair.

While in the illustrated three embodiments the CPU 50 judges whether the peripheral blood flow of the subject is abnormal, based on the attenuation-coefficient ratio $K_2/K_3$ or $K_1'/K_2'$, it is possible to determine an attenuation-coefficient ratio, $K_3/K_2$ or $K_2'/K_1'$, and use this ratio for evaluating the peripheral blood flow and/or displaying the graphical presentation of time-wise variation thereof.

Figure 2:
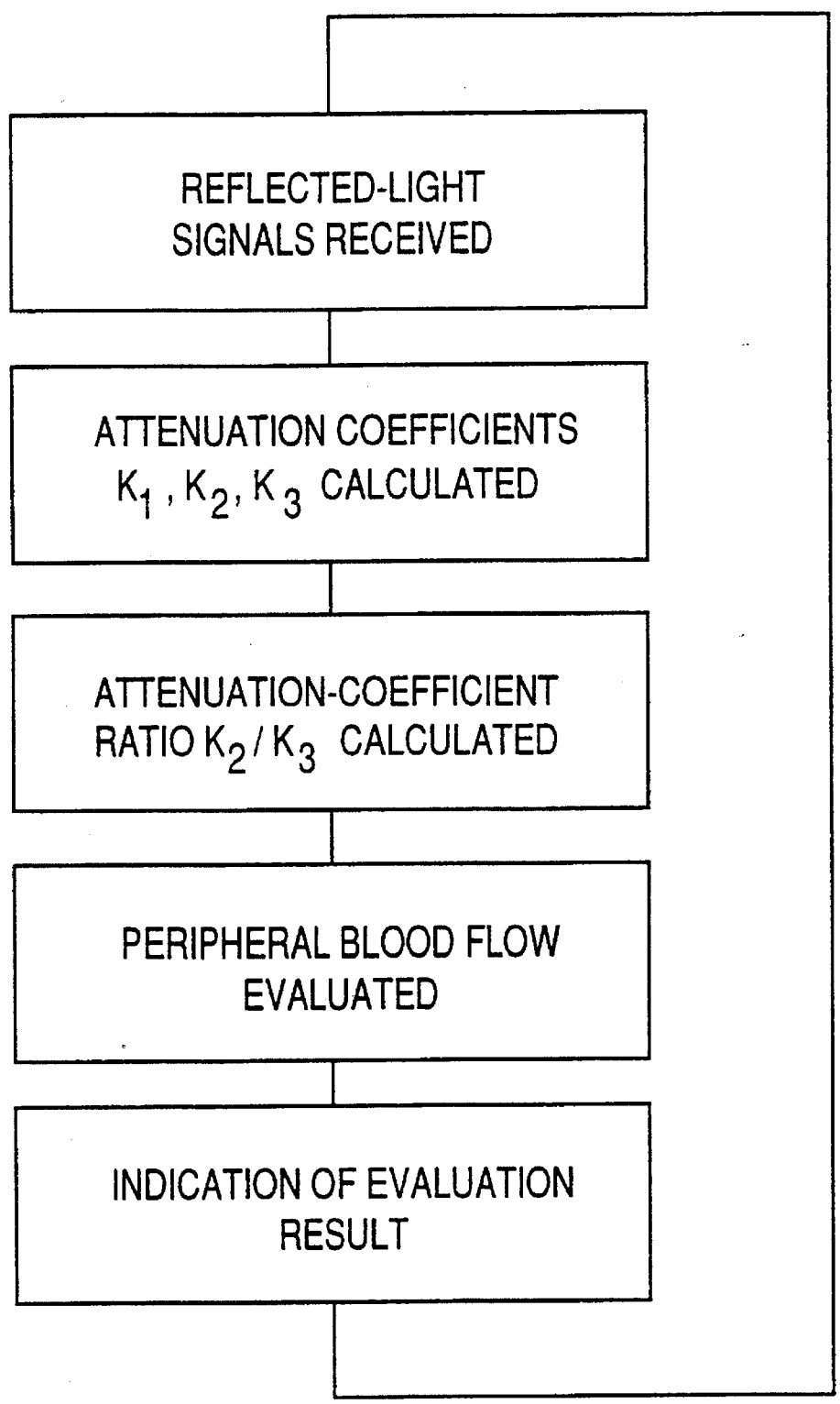
FIG. 2 is a flow chart representing a control program utilized by an arithmetic and control device of the apparatus of FIG. 1.

Although at Step S4 of FIG. 2 the CPU 50 judges, based on the amount of change $\Delta R$ of the attenuation-coefficient ratio $K_2/K_3$, whether the peripheral blood flow of the subject is normal or abnormal, i.e., evaluates the peripheral blood flow in two degrees, it is possible to adapt the apparatus to evaluate the peripheral blood flow in three or more degrees including, e.g., two or more degrees of abnormality, based on the change amount $\Delta R$.

In each of the first to third embodiments, the display 56 may be provided with additional display sections for indicating the current change amount $\Delta R$ and/or current total change amount W in digits.

Additionally, in each of the first to third embodiments, the CPU 50 may be designed to calculate a rate of change of the attenuation-coefficient ratio $K_2/K_3$, e.g., a gradient of the ratio-time curve thereof presented at the first area 58 of the display 56, and evaluate the subject's peripheral blood flow, in two or more degrees of normality and abnormality, based on the calculated rate of change. In the latter, case, the display 56 may indicate the calculated rate of change of the ratio in digits.

Although in the first and second embodiments the intensity $I_{R3}$ of the third reflected light is obtained from the point C located in the subcutaneous tissue 36, it is possible to obtain an intensity $I_{R3}$ of a third reflected light from a point C located away from the subcutaneous tissue 36. The present invention does not require more than that the point C be located at a depth different from that of the point B.

While in the first to third embodiments the three or two pairs of light-emitting and light-receiving elements are designed to have different element-to-element distances and the light-shading walls (24, 26, 28), (80, 82, 84), (98, 100) are disposed between those elements, for the purpose of receiving lights reflected from points of different depths in the skin tissue 12, those light-shading walls may be omitted. The "photon diffusion theory" disclosed at column 5, lines 7–30 of U.S. Pat. No. 4,867,557 states that, as the distance between a light-emitting and a light-receiving element changes, the depth of the way of transmission of the light from the light emitting element to the light receiving element also changes in the body tissue of a living body.

It is to be understood that the present invention may be embodied with other changes, improvements, and modifications that may occur to those skilled in the art without departing from the scope and spirit of the invention defined in the appended claims.

What is claimed is:

1. An apparatus for evaluating a peripheral blood flow of a living subject, comprising:

a reflection-type pulse detecting device including at least two pairs of light-emitting and light-receiving means provided such that a distance between the light-emitting and light-receiving means of one of said at least two pairs is different from a distance between the light-emitting and light-receiving means of the other, or each of the others, of said at least two pairs, said at least two pairs of light-emitting and light-receiving means being adapted to be opposed to a skin of said subject, the light-emitting means of each one of said at least two pairs emitting a light beam having a wavelength equal to a wavelength of a light beam emitted by the light-emitting means of the other, or each of the others, of said at least two pairs toward said skin so that the light-receiving means of said each pair receives the light which has been emitted from said light-emitting means of said each pair and subsequently reflected from said skin, and generates a reflected-light signal representing the reflected light received from said skin and containing a pulse wave signal resulting from flowing of blood in said skin;

attenuation-coefficient determining means for determining an attenuation coefficient of the light beam emitted by said light-emitting means of said each pair, based on (a) an intensity of the light beam which is emitted by said light-emitting means of said each pair and (b) an intensity of the light beam which has been emitted from said light-emitting means of said each pair, reflected from said skin of said subject, and subsequently received by said light-receiving means of said each pair; and peripheral-blood-flow evaluating means for evaluating said peripheral blood flow of said subject, based on a ratio of the attenuation coefficient of the light beam emitted by the light-emitting means of one of said at least two pairs, to the attenuation coefficient of the light beam emitted by the light-emitting means of the other or another of said at least two pairs.

2. An apparatus according to claim 1, wherein said peripheral-blood-flow evaluating means comprises means for judging whether said peripheral blood flow of said subject is abnormal, based on a change of said ratio of the attenuation coefficient of the light beam emitted by the light-emitting means of said one pair to the attenuation coefficient of the light beam emitted by the light-emitting means of said other pair or said another pair.

3. An apparatus according to claim 1, wherein said peripheral-blood-flow evaluating means comprises means for evaluating said peripheral blood flow of said subject as one of at least three degrees including one degree corresponding to normality of the peripheral blood flow and at least two degrees corresponding to abnormality of the peripheral blood flow, based on at least one of (a) an amount of change, and (b) a rate of change, of said ratio of the attenuation coefficient of the light beam emitted by the light-emitting means of said one pair to the attenuation coefficient of the light beam emitted by the light-emitting means of said other pair or said another pair.

4. An apparatus according to claim 1, wherein said pulse wave detecting device comprises a housing which supports said at least two pairs of light-emitting and light-receiving means such that said distance between the light-emitting and light-receiving means of said one pair is different from said distance between the light-emitting and light-receiving means of said other pair or said each of the other pairs.

5. An apparatus according to claim 1, wherein said pulse wave detecting device comprises:

a common light-emitting element which emits a common light beam toward said skin of said subject, said common light-emitting element being the light-emitting means of each of said at least two pairs of light-emitting and light-receiving means;

a first light-receiving element which receives a first reflected light beam which has been emitted by said common light-emitting element and subsequently reflected from a first depth of said skin, said first light-receiving element being the light-receiving means of one of said at least two pairs; and a second light-receiving element which receives a second reflected light beam which has been emitted by said common light-emitting element and subsequently reflected from a second depth of said skin different from said first depth, said second light-receiving element being the light-receiving means of the other, or another, of said at least two pairs, said common light-emitting element and said first and second light-receiving elements cooperating with each other to provide two pairs out of said at least two pairs of light-emitting and light-receiving means, said attenuation-coefficient determining means determining a first attenuation coefficient of said common light beam emitted by said common light-emitting element, based on (a) an intensity of said common light beam which is emitted by said common light-emitting element and (b) an intensity of the light beam which has been emitted from said common light-emitting element, reflected from said first depth of said skin, and subsequently received by said first light-receiving element, said attenuation-coefficient determining means determining a second attenuation coefficient of said common light beam emitted by said common light-emitting element, based on (a) said intensity of said common light beam which is emitted by said common light-emitting element and (b) an intensity of the light beam which has been emitted from said common light-emitting element, reflected from said second depth of said skin, and subsequently received by said second light-receiving element, said peripheral-blood-flow evaluating means evaluating said peripheral blood flow of said subject, based on a ratio of said first attenuation coefficient to said second attenuation coefficient.

6. An apparatus according to claim 1, wherein said pulse wave detecting device comprises:

a first light-emitting element which emits a first light beam toward said skin of said subject, said first light-emitting element being the light-emitting means of one of said at least two pairs of light-emitting and light-receiving means;

a second light-emitting element which emits a second light beam toward said skin, said second light emitting element beam the light-emitting means of the other, or another, or said at least two pairs;

a common light-receiving element which receives a first reflected light beam which has been emitted by said first light-emitting element and subsequently reflected from a first depth of said skin, and receives a second reflected light beam which has been emitted by said second light-emitting element and subsequently reflected from a second depth of said skin different from said first depth, said common light-receiving element beam the light-receiving means of each of said at least two pairs, said first and second light-emitting elements and said common light-receiving element cooperating with each other to provide two pairs out of said at least two pairs of light-emitting and light-receiving means, said attenuation-coefficient determining means determining a first attenuation coefficient, $K_1'$, of said first light beam emitted by said first light-emitting element, based on (a) an intensity, $I_{01}'$, of said first light beam which is emitted by said first light-emitting element and (b) an intensity $I_{R1}'$, of the light beam which has been emitted from said first light-emitting element, reflected from said first depth of said skin, and subsequently received by said common light-receiving element, said attenuation-coefficient determining means determining a second attenuation coefficient, $K_2'$, of said second light beam emitted by said second light-emitting element, based on (a) an intensity $I_{02}'$, of said second light beam which is emitted by said second light-emitting element and (b) an intensity, $I_{R2}'$, of the light beam which has been emitted from said second light-emitting element, reflected from said second depth of said skin, and subsequently received by said common light-receiving element, said peripheral-blood-flow evaluating means evaluating said peripheral blood flow of said subject, based on a ratio of said first attenuation coefficient $K_1'$ to said second attenuation coefficient $K_2'$.

7. An apparatus according to claim 6, wherein said attenuation-coefficient determining means determines said first and second attenuation coefficients $K_1'$, $K_2'$ according to following first and second expressions (1), (2), respectively:

$$K_1' = I_{R1}'/I_{01}' \tag{1}$$

$$K_2' = (I_{R2}'/I_{02}')/(I_{R1}'/I_{01}')^2 \tag{2}$$

said peripheral-blood-flow evaluating means evaluating said peripheral blood flow of said subject, based on at least one of a ratio, $K_1'/K_2'$, and a ratio, $K_2'/K_1'$.

8. An apparatus according to claim 1, wherein said pulse wave detecting device further comprises a plurality of light-shading walls each of which is provided between corresponding adjacent two means out of said at least two pairs of light-emitting and light-receiving means.

9. An apparatus for displaying a parameter relating to a peripheral blood flow of a living subject, comprising:

a reflection-type pulse wave detecting device including at least two pairs of light-emitting and light-receiving means provided such that a distance between the light-emitting and light-receiving means of one of said at least two pairs is different from a distance between the light-emitting and light-receiving means of the other, or each of the others, of said at least two pairs, said at least two pairs of light-emitting and light-receiving means being adapted to be opposed to a skin of said subject, so that the light-emitting means of each of said at least two pairs emits a light beam toward said skin and so that the light-receiving means of said each pair receives the light which has been emitted from said light-emitting means of said each pair and subsequently reflected from said skin, and generates a reflected-light signal representing the reflected light received from said skin and containing a pulse wave resulting from flowing of blood in said skin;

attenuation-coefficient determining means for determining an attenuation coefficient of the light beam emitted by said light-emitting means of said each pair, based on (a) an intensity of the light beam which is emitted by said light-emitting means of said each pair and (b) an intensity of the light beam which has been emitted from said light-emitting means of said each pair, reflected from said skin of said subject, and subsequently received by said light-receiving means of said each pair; and a display which displays, as a change of said parameter, a change of a ratio of the attenuation coefficient of the light beam emitted by the light-emitting means of one of said at least two pairs, to the attenuation coefficient of the light beam emitted by the light-emitting means of the other or another of said at least two pairs.

10. An apparatus according to claim 9, wherein said display comprises a first area for displaying a graphical curve representing said change of said ratio of the attenuation coefficient of the light beam emitted by the light-emitting means of said one pair to the attenuation coefficient of the light beam emitted by the light-emitting means of said other pair or said another pair.

11. An apparatus according to claim 9, further comprising peripheral-blood-flow evaluating means for evaluating said peripheral blood flow of said subject, said ratio being as said parameter.

12. An apparatus according to claim 11, wherein said display comprises a second area for displaying a result of evaluation of said peripheral-blood-flow evaluating means.

13. An apparatus according to claim 12, wherein said display comprises means for displaying, in said area, said result of evaluation of said peripheral-blood-flow evaluating means, together with a time when said result is obtained by said peripheral-blood-flow evaluating means.

14. An apparatus according to claim 9 wherein said light-emitting means of each of said at least two pairs of light-emitting and light-receiving means of said pulse wave detecting device comprises means for emitting a red or infrared light having a wavelength not less than about 660 nm.

15. An apparatus according to claim 9, wherein said light-emitting means of said at least two pairs of light-emitting and light-receiving means of said pulse wave detecting device comprise at least one light emiting diode chip.

16. An apparatus according to claim 9, wherein said light-receiving means said at least two pairs of light-emitting and light-receiving means of said pulse wave detecting device comprise at least one of a photodiode chip and a phototransistor chip.

17. An apparatus according to claim 9, wherein said pulse wave detecting device comprises a housing which supports said at least two pairs of light-emitting and light-receiving means such that said distance between the light-emitting and light-receiving means of said one pair is different from said distance between the light-emitting and light-receiving means of said other pair or said each of the other pairs, said housing having a recess for receiving said light-emitting and light-receiving means.

18. An apparatus according to claim 17, wherein said pulse wave detecting device further comprising:

a plurality of light-shading walls received in said recess of said housing such that each of said light-shading walls is provided between corresponding adjacent two means of said at least two pairs of light-emitting and light-receiving means; and a transparent resin body which fills said recess of said housing over said at least two pairs of light-emitting and light-receiving means and said plurality of light-shading walls.

19. An apparatus according to claim 9, wherein said at least two pairs of light-emitting and light-receiving means of said pulse wave detecting device comprise three pairs of light-emitting and light-receiving means, said attenuation-coefficient determining means determining a first, a second, and a third attenuation coefficient, $K_1$, $K_2$, $K_3$ of a first, a second, and a third light beam emitted by the respective light-emitting means of a first, a second, and a third pair of said three pairs, based on (a) a first, a second, and a third intensity, $I_{01}$, $I_{02}$, $I_{03}$ of the first, second, and third light beams which are emitted by said respective light-emitting means of said first, second, and third pairs and (b) a first, a second, and a third intensity, $I_{R1}$, $I_{R2}$, $I_{R3}$ of the respective lights which have been emitted from said respective light-emitting means of said first, second, and third pairs, reflected from a first, a second, and a third depth in said skin of said subject wherein said second depth is greater than said first depth and smaller than said third depth, and subsequently received by the respective light-receiving means of said first, second, and third pairs, according to following first, second, and third expressions (3), (4), (5), respectively:

$$K_1 = I_{R1}/I_{01} \tag{3}$$

$$K_2 = (I_{R2}/I_{02})/(I_{R1}/I_{01})^2 \tag{4}$$

$$K_3 = (I_{R3}/I_{03})(I_{R1}/I_{01})^2/(I_{R2}/I_{02})^2 \tag{5}$$

said display displaying a change of at least one of a ratio, $K_2/K_3$, and a ratio, $K_3/K_2$.

20. An apparatus according to claim 9, wherein said pulse wave detecting device comprises:

a common light-emitting element which emits a common light beam toward said skin of said subject, said common light-emitting element being the light-emitting means of each of said at least two pairs of light-emitting and light-receiving means;

a first light-receiving element which receives a first reflected light beam which has been emitted by said common light-emitting element and subsequently reflected from a first depth of said skin, said first light-receiving element being the light-receiving means of one of said at least two pairs; and a second light-receiving element which receives a second reflected light beam which has been emitted by said common light-emitting element and subsequently reflected from a second depth of said skin different from said first depth, said second light-receiving element being the light-receiving means of the other, or another, of said at least two pairs, said common light-emitting element and said first and second light-receiving elements cooperating with each other to provide two pairs out of said at least two pairs of light-emitting and light-receiving means, said attenuation-coefficient determining means determining a first attenuation coefficient of said common light beam emitted by said common light-emitting element, based on (a) an intensity of said common light beam which is emitted by said common light-emitting element and (b) an intensity of the light beam which has been emitted from said common light-emitting element, reflected from said first depth of said skin, and subsequently received by said first light-receiving element, said attenuation-coefficient determining means determining a second attenuation coefficient of said common light beam emitted by said common light-emitting element, based on (a) said intensity of said common light beam which is emitted by said common light-emitting element and (b) an intensity of the light beam which has been emitted from said common light-emitting element, reflected from said second depth of said skin, and subsequently received by said second light-receiving element, said peripheral-blood-flow evaluating means evaluating said peripheral blood flow of said subject, based on a ratio of said first attenuation coefficient to said second attenuation coefficient.

21. An apparatus according to claim 9, wherein said pulse wave detecting device comprises:

a first light-emitting element which emits a first light beam toward said skin of said subject, said first light-emitting element being the light-emitting means of one of said at least two pairs of light-emitting and light-receiving means;

a second light-emitting element which emits a second light beam toward said skin, said second light-emitting element being the light-emitting means of the other, or another, of said at least two pairs;

a common light-receiving element which receives a first reflected light beam which has been emitted by said first light-emitting element and subsequently reflected from a first depth of said skin, and receives a second reflected light beam which has been emitted by said second light-emitting element and subsequently reflected from a second depth of said skin different from said first depth, said common light-receiving element being the light-receiving means of each of said at least two pairs, said first and second light-emitting elements and said common light-receiving element cooperating with each other to provide two pairs out of said at least two pairs of light-emitting and light-receiving means, said attenuation-coefficient determining means determining a first attenuation coefficient of said first light beam emitted by said first light-emitting element, based on (a) an intensity of said first light beam which is emitted by said first light-emitting element and (b) an intensity of the light beam which has been emitted from said first light-emitting element, reflected from said first depth of said skin, and subsequently received by said common light-receiving element, said attenuation-coefficient determining means determining a second attenuation coefficient of said second light beam emitted by said second light-emitting element, based on (a) an intensity of said second light beam which is emitted by said second light-emitting element and (b) an intensity of the light beam which has been emitted from said second light-emitting element, reflected from said second depth of said skin, and subsequently received by said common light-receiving element, said peripheral-blood-flow evaluating means evaluating said peripheral blood flow of said subject, based on a ratio of said first attenuation coefficient to said second attenuation coefficient.

22. An apparatus for evaluating a peripheral blood flow of a living subject, comprising:

a reflection-type pulse wave detecting device including at least two pairs of light-emitting and light-receiving means provided such that a distance between the light-emitting and light-receiving means of one of said at least two pairs is different from a distance between the light-emitting and light-receiving means of the other, or each of the others, of said at least two pairs, said at least two pairs of light-emitting and light-receiving means being adapted to be opposed to a skin of said subject, so that the light-emitting means of each of said at least two pairs emits a light beam toward said skin and so that the light-receiving means of said each pair receives the light beam which has been emitted from said light-emitting means of said each pair and subsequently reflected from said skin, and generates a reflected-light signal representing the reflected light received from said skin and containing a pulse wave resulting from flowing of blood in said skin;

attenuation-coefficient determining means for determining an attenuation coefficient of the light beam emitted by said light-emitting means of said each pair, based on (a) an intensity of the light beam which is emitted by said light-emitting means of said each pair and (b) an intensity of the light beam which has been emitted from said light-emitting means element of said each pair, reflected from said skin of said subject, and subsequently received by said light-receiving means element of said each pair; and peripheral-blood-flow evaluating means for evaluating said peripheral blood flow of said subject, based on a ratio of the attenuation coefficient of the light beam emitted by the light-emitting means element of one of said at least two pairs, to the attenuation coefficient of the light beam emitted by the light-emitting means of the other or another of said at least two pairs, wherein said peripheral-blood-flow evaluating means comprises means for judging whether said peripheral blood flow of said subject is abnormal, based on a change of said ratio of the attenuation coefficient of the light beam emitted by the light-emitting means of said one pair to the attenuation coefficient of the light beam emitted by the light-emitting means of said other pair or said another pair.

* * * * *